(12) United States Patent
Belotserkovsky (10) Patent No.: US 8,276,465 B2
(45) Date of Patent: Oct. 2, 2012

(54) URINE FLOW MONITORING DEVICE AND METHOD

(76) Inventor: Edward Belotserkovsky, San Francisco, CA (US)

( * ) Notice: Subject to any disclaimer, the term of this patent is extended or adjusted under 35 U.S.C. 154(b) by 66 days.

(21) Appl. No.: 12/877,289

(22) Filed: Sep. 8, 2010

(65) Prior Publication Data

US 2012/0048033 A1    Mar. 1, 2012

Related U.S. Application Data

(60) Provisional application No. 61/353,216, filed on Jun. 10, 2010.

(51) Int. Cl.
*G01F 1/20* (2006.01)
(52) U.S. Cl. ..................................... 73/861.18
(58) Field of Classification Search ............ 73/861, 73/861.18; 600/586; 424/195.15
See application file for complete search history.

(56) References Cited

U.S. PATENT DOCUMENTS

| | | |
|---|---|---|
| 4,098,128 A | 7/1978 | Baumert |
| 4,343,316 A | 8/1982 | Jespersen |
| 4,438,526 A | 3/1984 | Thomalla |
| 4,532,936 A | 8/1985 | LeVeen |
| 4,534,361 A | 8/1985 | Berger |
| 4,554,687 A | 11/1985 | Carter |
| 4,658,834 A | 4/1987 | Blankenship |
| 4,965,833 A | 10/1990 | McGregor |
| 5,078,012 A | 1/1992 | Ding |
| 5,125,268 A | 6/1992 | Caron |
| 5,213,108 A | 5/1993 | Bredesen |
| 5,218,971 A | 6/1993 | Minami |
| 5,377,101 A | 12/1994 | Rollema |
| 5,384,856 A | 1/1995 | Kyouno et al. |
| 5,539,831 A | 7/1996 | Harley |
| 5,565,639 A | 10/1996 | Bae |
| 5,596,150 A | 1/1997 | Arndt |
| 5,831,528 A | 11/1998 | Cecic |
| 5,938,738 A | 8/1999 | Mu-Teng |
| 5,983,253 A | 11/1999 | Fischer |

(Continued)

FOREIGN PATENT DOCUMENTS

WO    2008306962 A2    3/2008

(Continued)

OTHER PUBLICATIONS

Life-Tech UROVISION Video Urodynamics Specification sheet (2 pages).

(Continued)

*Primary Examiner* — Jewel V Thompson
(74) *Attorney, Agent, or Firm* — Cascio & Zervas (57) ABSTRACT

The unique characteristic sounds produced by urine as it impacts the surface of the water in a toilet are used to monitor men's urinary flow pattern and its dynamics. By detecting the intensity at selected acoustic frequencies, it is possible to accurately and precisely measure the urine flow rate. Techniques for analyzing urine flow and its dynamics employ sound levels that are detected at two or more distinct frequency regions or channels of the sound spectrum. One frequency region that is designated the measurement channel is where the sound measurement intensity strongly depends on urine flow levels. Another frequency region that is designated the reference channel is where the sound measurement intensity is not dependent on urine flow levels. By using a combination of measurements from the measurement channel and the reference channel, the urine-flow monitoring apparatus compensates for variations in operating conditions and other factors during use.

31 Claims, 6 Drawing Sheets

U.S. PATENT DOCUMENTS

| | | |
|---|---|---|
| 6,183,561 B1 | 2/2001 | Belotserkovsky |
| 6,546,437 B1 | 4/2003 | Grimsrud |
| 6,644,973 B2 | 11/2003 | Oster |
| 6,650,757 B1 | 11/2003 | Zhou |
| 6,746,131 B1 | 6/2004 | Goldstein |
| 6,754,355 B2 | 6/2004 | Stetzler |
| 6,904,809 B1 | 6/2005 | Aundal |
| 6,931,943 B1 | 8/2005 | Aundal |
| 7,416,542 B2 | 8/2008 | Aundal |
| 7,486,976 B1 | 2/2009 | Belotserkovsky |
| 7,488,292 B2 | 2/2009 | Adachi |
| 7,597,910 B2 | 10/2009 | McDowell |
| 7,645,286 B2 | 1/2010 | Catanese |
| 7,758,519 B2 | 7/2010 | Brohan et al. |
| 2001/0042150 A1 | 11/2001 | Moroz et al. |
| 2008/0082022 A1 | 4/2008 | Brohan et al. |
| 2008/0275366 A1 | 11/2008 | Brohan |
| 2008/0312538 A1* | 12/2008 | Shahar et al. ............ 600/459 |
| 2010/0262517 A1 | 10/2010 | Woods |
| 2011/0125061 A1* | 5/2011 | Shahar et al. ............ 600/586 |

FOREIGN PATENT DOCUMENTS

WO 2009138979 A1 11/2009

OTHER PUBLICATIONS

Medispec Urospec Brochure (2 pages).
Peter Zvara, TeleMed Test, from Website:www.sonouroflow.com. pp. 1-17 Sep. 15, 2010.
D.L.Hitt, Urinary Flow Measurements Via Acoustic Signatures with Application to Telemedicine, Am. Institute of Aeronautics and Astronautics, pp. 1-10.
Belotserkovsky, Edward Urine Flow Monitoring Device and Method PCT/US2011/64940; Written Opinion Mar. 15, 2012.
Keitzer W. A. The Voiding Audiograph: A New Voiding Test The Journal of Urology vol. 96, No. 3, Sep. 1966, pp. 404-410 Sections "The Voiding Audiograph" and "Voiding Resistence", Figs. 5-7.
Idzenga T Toward an Acoustic Noninvasive Diagnosis of Urinary Bladder Outlet Obstruction vol. 55, No. 6, Jun. 1, 2008 pp. 1764-1771 Sections "I. Introduction" and "IV. Conclusion".

* cited by examiner

URINE FLOW MONITORING DEVICE AND METHOD

REFERENCE TO RELATED APPLICATIONS

This application claims priority, to U.S. Provisional Application 61/353,216 that was filed on Jun. 10, 2010.

FIELD OF THE INVENTION

The present invention generally relates to a medical apparatus for monitoring the discharge of urine by an individual. The apparatus gauges the volumetric flow and flow dynamics of the discharge, analyzes the data and displays the results.

BACKGROUND OF THE INVENTION

The prostate is a gland of the male reproductive system that is located in front of the rectum and just below the bladder. The prostate, comprised largely of muscular and glandular tissue, is wrapped around the urethra, which carries urine from the bladder out through the tip of the penis. Disorders of the prostate are fairly common during the aging process and include prostatitis, benign prostatic hyperplasia (BPH), and adenoma of the prostate, or prostate cancer. Prostatitis, which may or may not be the result of an infection, is generally defined as an inflammation of the prostate. Symptoms associated with prostatitis are pain, voiding symptoms such as nocturia, frequency and urgency of urination, incomplete voiding, and decreased force and/or intermittency of the urinary stream, impotence, and infertility.

Benign prostatic hyperplasia (BPH) is a noncancerous enlargement of the prostate and is common in men over age 40. Symptoms associated with BPH are similar to those observed with prostatitis. Prostate cancer, i.e., adenocarcinoma of the prostate, is the most common malignancy in men greater than 50 years in the US. The incidence increases with each decade of life. Prostate cancer is generally slowly progressive and may cause no symptoms. In late disease, symptoms of bladder outlet obstruction, urethral obstruction, and hematuria may appear and metastasis to the bone may occur.

Diagnosis of urological disorders is often facilitated by a patient's urine flow rate data. Urological disorders such as an obstruction in the lower urological tract or neurotic bladder can be detected by studying the patient's urine flow rate as it varies from the beginning of voiding to the end and the total volume of urine voided. This data can be compared to the mean data for an individual of the same sex and age to help determine the degree of urethral stricture.

Urine flow data is also useful in diagnosing prostrate enlargement. Prostrate enlargement usually occurs gradually with no noticeable impairment to the patient. Merely observing the patient void will usually not enable the urologist or physician to accurately assess the degree of prostate enlargement. However, by observing histograms of the urine flow, the urologist or physician can usually detect the degree of prostrate enlargement and the necessary procedures to be undertaken to correct the disorder. In addition, post-operative urine flow data provides an excellent way of assessing the benefit achieved by surgery.

A variety of urine flow meters for providing urine flow data is presently commercially available. For example, mechanical urine flow meter devices usually comprise a container having a graduated scale for indicating the volume of urine within the container. Urine flow is detected by observing the change in volume as the patient voids into the container. Electrical urine flow meters for providing urine flow data have been developed. These devices may have a urine velocity-measuring apparatus in the form of a urine flow receptacle with a paddle wheel journaled therein. The paddle wheel is mechanically linked to a generator which produces an output voltage which is displayed on a volt meter. The velocity of the urine stream impinging on the paddle wheel determines the paddle wheel velocity and therefore the output voltage of the generator. Other urine flow devices include a urine-receiving receptacle that has a pair of parallel spaced-apart rods or strips disposed therein. The rods or strips are electrically connected to a capacitance sensing circuit. As the volume of urine within the receptacle increases, the capacitance between the rods also increases so that by measuring the rate of change of the capacitance, an indication of the urine flow may be obtained.

As is apparent, current urine flow meters are complex and often require the assistance of a clinician for proper use; moreover, the devices require a high degree of maintenance. Furthermore, since urine contacts components in each of the meters, those components must be cleaned following each use. Therefore, a need exists for a reliable, low maintenance urine flow meter.

SUMMARY OF THE INVENTION

The present invention is based in part on the recognition that during urination (or voiding process) the unique characteristic sounds that are produced by the urine as it impacts the surface of the water in a toilet or urinal can be used to monitor the person's urinary flow pattern and its dynamics. Specifically, because the sound's intensity (loudness) and spectrum depend on the urine flow level, by detecting the intensity at selected acoustic frequencies, it is possible to accurately and precisely measure the urine flow rate.

In a preferred embodiment, the present invention is directed to techniques for analyzing urine flow and its dynamics by using sound levels that are detected at two or more distinct frequency regions or channels of the sound spectrum. One frequency region that is designated the measurement channel is where the sound measurement intensity or output strongly depends on urine flow levels. Another frequency region that is designated the reference channel is where the sound measurement intensity is not dependent on urine flow levels. By using a combination of measurements from the measurement channel and the reference channel, the urine flow monitoring apparatus of the present invention compensates for variations in operating conditions and other factors during use.

In one aspect, the invention is directed to an apparatus for measuring urine flow that includes:

a microphone for detecting acoustical sound that is generated as urine impacts a liquid surface and converting it into electrical signals;

an amplifier connected to the microphone to amplify electrical signals therefrom; and means for analyzing signal components to generate urine flow level data.

In another aspect, the invention is directed to a system for analyzing the urinary flow patterns of a male patient as he voids that includes:

a microphone for converting acoustic energy, that is generated as urine from the patient impacts a surface, into eledrical signals;

an amplifier connected to the microphone to amplify electrical signals therefrom; and means for analyzing signal components to identify urinary flow patterns.

In a further aspect, the invention is directed to a portable device designed to be worn on a male patient for measuring urinary flow patterns as he voids that includes:

a microphone for converting acoustic energy, that is generated as urine from the patient impacts a surface, into electrical signals;

an amplifier connected to the microphone to amplify electrical signals to yield amplified electrical signals; and means for processing signal components to generate signals that are representative of urinary flow data.

In yet a further aspect, the invention is directed to a method for measuring urinary flow from a male patient as he voids that includes the steps of:

(a) detecting acoustic energy that is generated as urine impacts a liquid surface;

(b) converting the acoustic into electrical signals; and (c) processing the electrical signals to generate output signals that represent urinary flow data for the male patient.

In preferred embodiment of the urine flow-monitoring device, a filter is employed to extract filtered signals by filtering amplified signals from the amplifier. An analogue-to-digital converter can be employed to convert amplified signals into digital form for analysis.

DETAIL DESCRIPTION OF PREFERRED EMBODIMENTS

Figure 1:
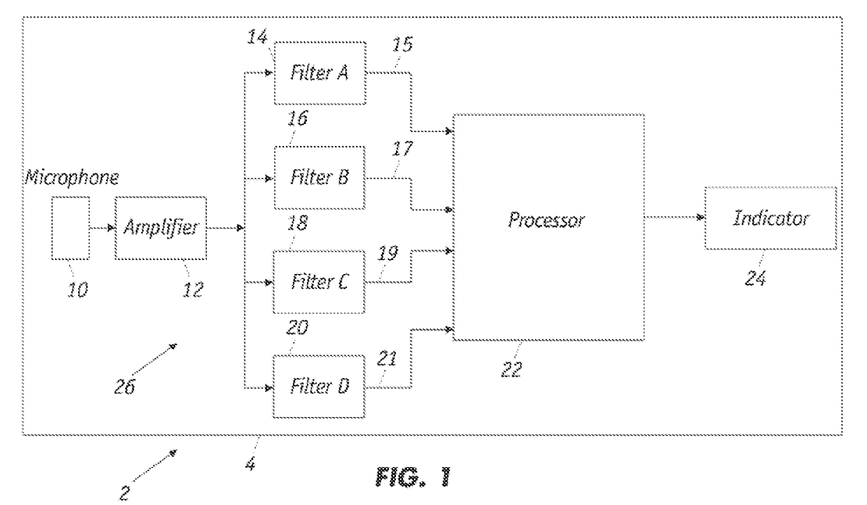
FIGS. 1 to 6 are schematic of alternative configurations of the urine flow monitoring device.

As shown in FIG. 1, the medical urine flow monitoring device 2 includes a housing 4 that encloses a microphone 10, amplifier 12, a bank of filters 26 that includes filters 14, 16, 18, and 20, a signal processor 22 and an output indicator 24. Electrical signals from microphone 10, which can be omnidirectional or unidirectional microphone(s), are amplified by amplifier 12 before being passed through a plurality of filters 14, 16, 18 and 20, that produce filtered signals 15, 17, 19, and 21, respectively. As further described herein, the bank of filters 26 serves to select the filtered signals of the desired frequency ranges to be analyzed by processor 22. The filters comprise one or more of a high-pass, low-pass, band-pass, and band-stop filter, for example, which are designated as Filters A, B, C and D, respectively. FIG. 1 depicts a four-channel urine flow-monitoring device with each channel employing a different type of filter. As further described herein, preferably one or more of the channels measure sound with frequencies in a measurement range and one or more of the channels measure sound with frequencies in a reference range. The choice of filters depends on, among other things, the filtered frequencies of interest. The filters may be fixed or variable. Housing 4 can be constructed as a portable unit that can secured to a person's belt or it can be designed as a permanent wall unit that can be mounted on the bathroom wall at home, the hospital or doctor's office.

Figure 2:
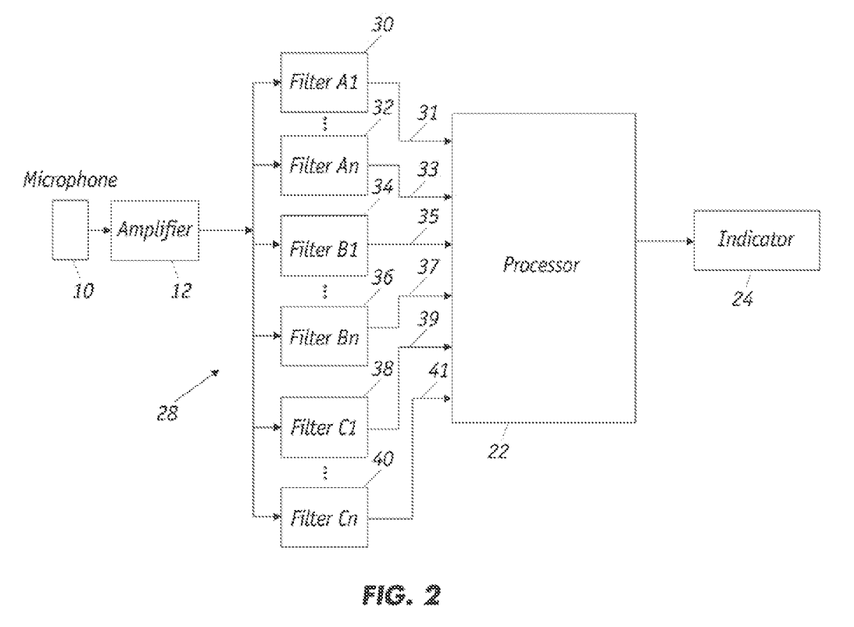

FIG. 2 depicts a multiple channel urine flow-monitoring device that includes a microphone 10, amplifier 12, a bank of filters 28, a signal processor 22 and an output indicator 24. This embodiment illustrates a device where multiple channels use the same type of filters, preferably with different frequencies of operation, and is expected to be more accurate than the device of FIG. 1. Filters 30 and 32, which produce filtered signals 31 and 33, respectively, employ filters of type A. Filters 34 and 36, which produce filtered signals 35 and 37, respectively, employ filters of type B. And finally, filters 38 and 40, which produce filtered signals 39 and 41, respectively, employ filters of type C.

Figure 3:
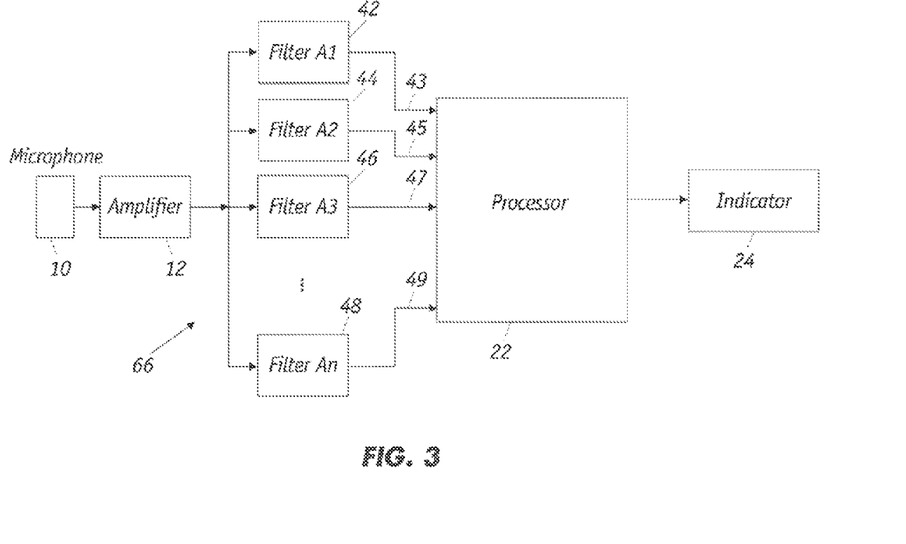

FIG. 3 depicts a multiple channel urine flow-monitoring device that includes a microphone 10, amplifier 12, a bank of filters 66, a signal processor 22 and an output indicator 24. This embodiment illustrates a multiple channel device that uses the same type of filters. Specifically, filters 42, 44, 46, and 48, which produce filtered signals 43, 45, 47, and 49, respectively, each employs a filter of type A.

Figure 4:
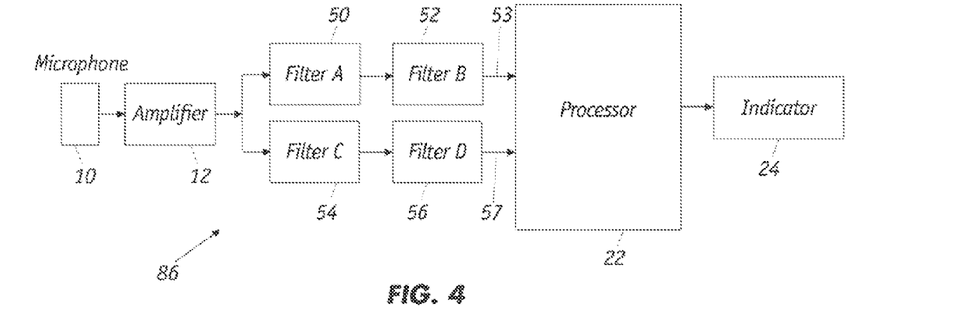

FIG. 4 depicts a multiple channel urine flow-monitoring device that includes a microphone 10, amplifier 12, a bank of filters 86, a signal processor 22 and an output indicator 24. This embodiment illustrates a device where at least one of the channels uses two or more filters. Specifically, amplified signals are passed through two channels: the first comprising filters 50, 52 and the second comprising filters 54, 56, to produce filtered signals 53 and 57 that are processed by processor 22. Four different types of filters, designated A, B, C and D, are employed but it is understood different combinations of filters can be used.

Figure 5:
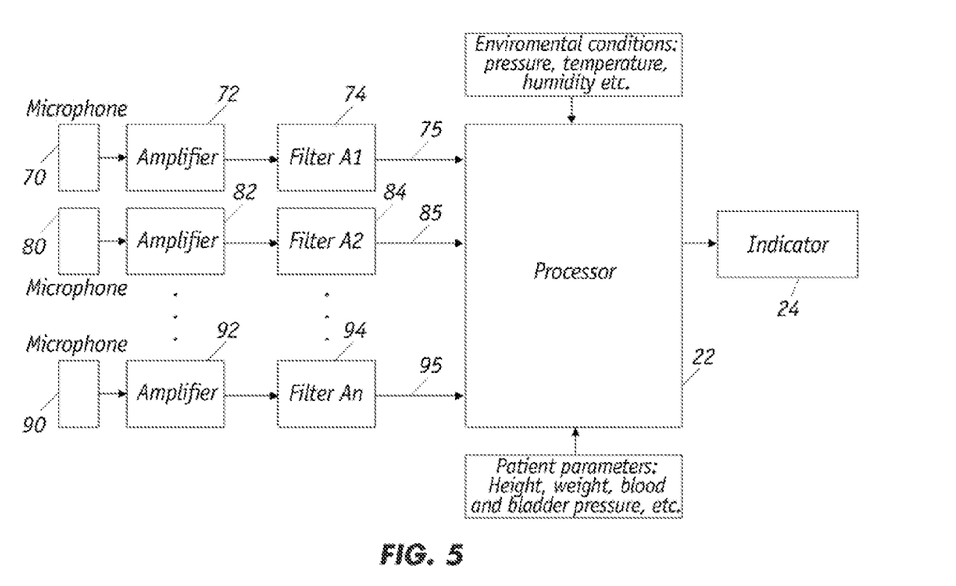

FIG. 5 depicts a multiple channel urine flow-monitoring device that employs a microphone for each channel for improved performance. Each microphone can be configured for sound acquisition in a particular frequency range. Specifically the first channel includes microphone 70, amplifier 72 and filter 74; the second channel includes microphone 80, amplifier 82 and filter 84; and the third channel includes microphone 90, amplifier 92 and filter 94. Processor 22 analyzes filtered signals 75, 85, and 95 to generate programmed outputs that are displayed in indicator 24. Environment conditions such as pressure, temperature, humidity and other factors, such as urine receptacle geometry and size and water depth, that can influence the intensity and/or frequency of the sound detected are entered into processor 22. The patient's medical history including his height, weight, blood pressure, bladder pressure and other health parameters can also be entered into the processor.

Figure 6:
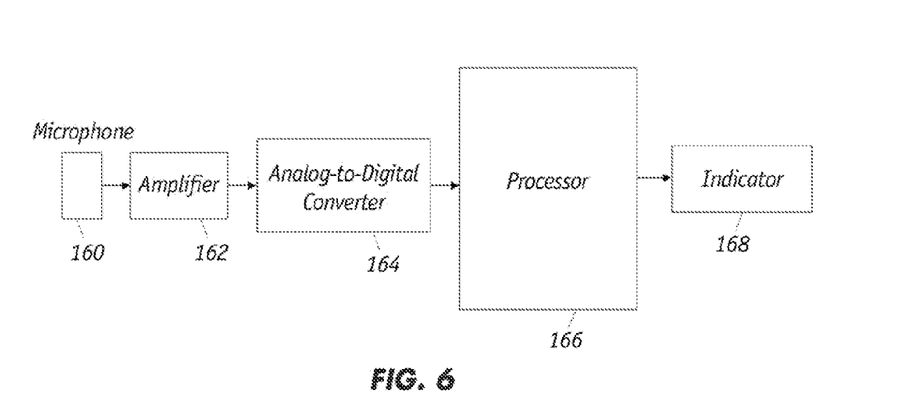

Finally, FIG. 6 depicts a urine-flow monitoring device that includes a microphone 160, amplifier 162, an analogue-to-digital converter 164, a signal processor 166 and an indicator 168. The analogue-to-digital converter converts amplified microphone signal into digital form. The processor digitally filters the signal components of interest and generates outputs that are displayed by the indicator. As mentioned above, environment conditions and the patient's physical condition and medical history can be entered into the processor.

Figure 7:
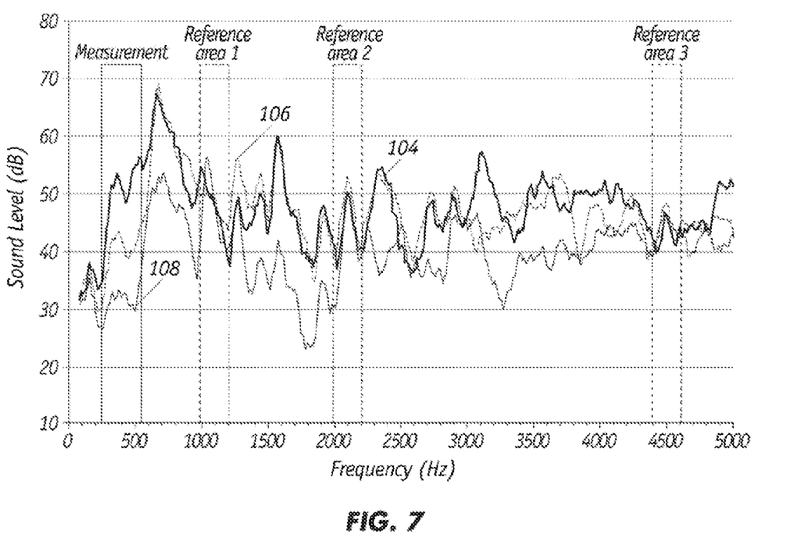
FIG. 7 is a graph of sound spectra (loudness in decibel vs. frequency) that are generated by the impact of urine on water.

When a male patient urinates, a continuous, distinctive sound is produced as the urine impacts the water in the toilet. Three representative sound spectra captured by a microphone during urinations are presented in FIG. 7. Spectrum 104 depicts the measured response in the case where the urination exhibited "strong" volumetric flow, spectrum 106 was the response for "medium" volumetric flow, and spectrum 108 was the response for "weak" volumetric flow. As is apparent, the sound level signal in the frequency range of 250-550 Hz, which is designated a measurement range, strongly depends on a flow level, whereas the sound level signals in the frequency ranges of 1000-1200 Hz, 2000-2200 Hz, and 4400-4600 Hz, which are designated as reference ranges, are significantly less so. Thus, by monitoring the loudness of the sound caused by urination at a frequency where the measured sound level depends on the flow level, it is possible to measure the urine flow rate. The intensity of the sound that is acquired by the microphone is influenced by a number of extraneous factors including the relative position and distance of the microphone to the site of impact as well as environmental conditions. Thus, in a preferred embodiment, the urine flow monitoring device has at least two channels: one or more measurement channels that measures sound at a frequency within the range of 250-550 Hz and one or more reference channels that measures sound at a frequency within the range of 1000-1200, Hz 2000-2200 Hz, and/or 4400-4600 Hz. As described further herein, by analyzing the difference between the decibel values of the measurement and reference signals or the ratio between the measurement and reference signals, the urine flow rate and other data can be determined in a manner wherein measurement variations caused by the extraneous factors are significantly reduced or eliminated. The urine flow-monitoring device can use one or more of the reference ranges.

Figure 8A:
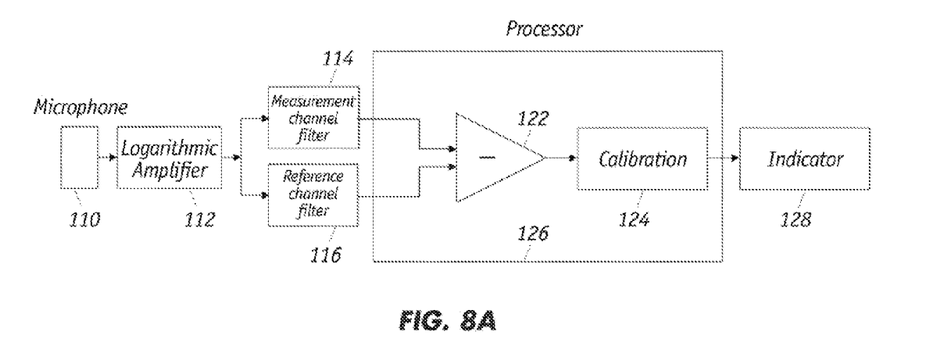
FIGS. 8A and 8B are schematic configurations of the urine flow monitoring device in which the sound is measured using linear and logarithmic amplifiers, respectively.

The device of the present invention can use, for instance, either logarithmic or linear amplifiers. The urine flow-monitoring device shown in FIG. 8A has a logarithmic amplifier and is configured to process sound levels in decibels and it includes a microphone 110, amplifier 112, a measurement channel, filter 114, a reference channel filter 116, a processor 126 and an indicator 128. Amplified signals are passed through the measurement and reference channel filters and the difference in the decibel readings is calculated in step 122; signal components are stored, analyzed, and converted by the processor's calibration unit 124 into signals for indicator 128. It should be noted that in operation preferably readings are continuously derived from both the measurement and reference channels from the beginning to the end of the voiding process, stored and then processed to yield information about the patient's urine flow pattern and to provide an evaluation of the patient's condition.

Figure 8B:
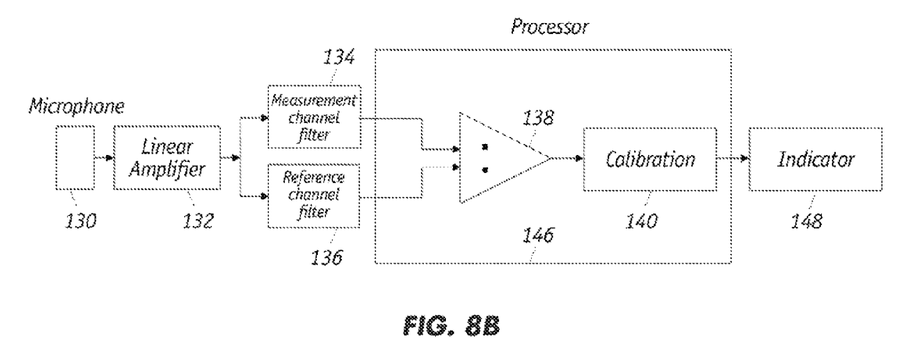

The urine flow-monitoring device shown in FIG. 8B has a linear amplifier and is configured to process sound levels in linear units and it includes a microphone 130, amplifier 132, a measurement channel filter 134, a reference channel filter 136, a processor 146 and an indicator 148. Amplified signals are passed through the measurement and reference channel filters and the ratios of the filtered signal readings are calculated in step 138 which are stored, analyzed, and converted by the processor's calibration unit 140 into signals for indicator 148.

One method of calibrating the urine flow-monitoring device is to measure the sound with the measurement channel and reference channel at different urine flow rates under controlled flow conditions. Another method is based on the total urine volume voided during the calibration. For example, as the flow impacts the water in a toilet, the urine flow-monitoring device captures the sound and records the corresponding sound levels of the measurement channel M(t) and reference channel R(t). The output signal, which is calculated as the difference between the measurement and reference channels: D(t)=M(t)−R(t), and which is proportional to the flow rate is calibrated with respect to the total urine volume $V_0$. It is known that the area under the function D(t) corresponds to the total urine volume $V_0$, which can be calculated by the equation $V_0 = \int_{t_1}^{t_2}(A \cdot D(t)+B)dt$, where A and B are the calibration coefficients, and $t_1$ and $t_2$ are times of the beginning and the end of the urination process. Thus, calibrating the device only requires that coefficients A and B be determined. If a linear amplifier is used, the total voided urine volume is calculated as $V_0 = \int_{t_1}^{t_2}(C \cdot F(t)+D)dt$, where F(t) is the ratio between measurement signal M(1) and reference signal R(t): F(t)=M(t)/R(t), and C and D are the calibration coefficients. Polynomial dependencies of the higher order, if needed, can also be used to calibrate the device. As is apparent, the urine flow-monitoring device can employ multiple measurement channels and multiple reference channels and the output signals derived from each device can be similarly calibrated.

Environmental conditions such as temperature and pressure can affect measurements of the urine-flow monitoring device. A device can be calibrated under different conditions at the factory so that when a patient uses the device he can set the appropriate operating conditions of temperature, pressure etc. so that the correct calibration constants are used.

Figure 9:
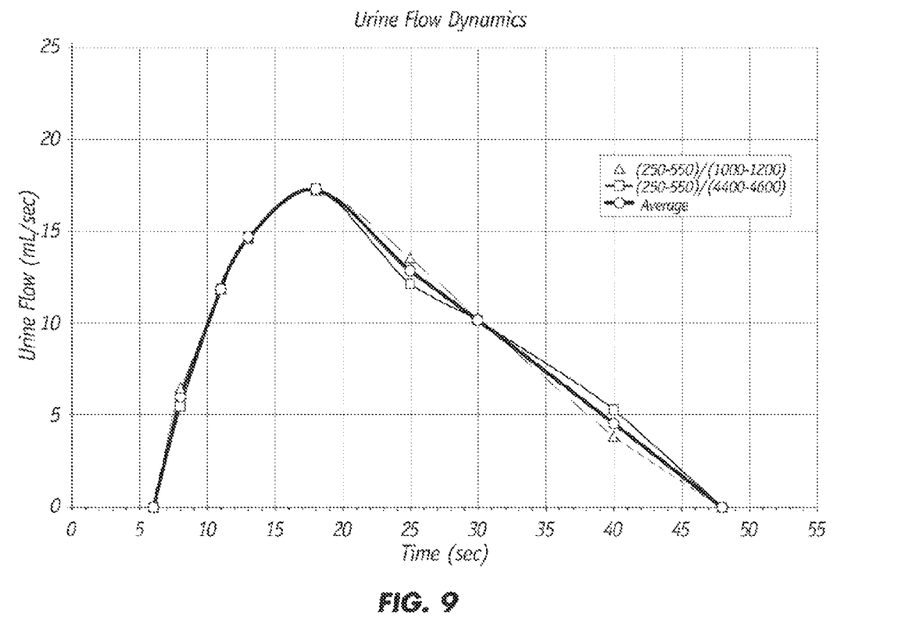
FIG. 9 is a representative graph of the flow dynamics (urine flow rate vs. time) during voiding.

A urine-flow monitoring device that included a single microphone, an amplifier, a measurement channel, with a band pass filter, and two reference channels, each with a band pass filter, was constructed. The measurement channel processed sound in the frequency range of 250-550 Hz and two reference channels processed sound in the frequency ranges of 1000-1200 Hz and 4400-4600 Hz. The device was calibrated whereby signals from all three channels were generated over the course of the voiding process in which a total urine volume of about 380 mL was released. The device was configured to provide two flow rate measurements, both employing the measurement channel but one using the first reference channel and the second using the second reference channel. FIG. 9 is the urine flow dynamics as measured by the device, along with the average between two readings. The results show that the two reference channels yield comparable flow measurements.

The urine-flow monitoring device can be programmed with data to enable the unit to display urinary flow information, based on analysis and classification, for the user. For example, analysis of the filtered signals can yield information concerning the patient's voiding patterns, including: mean dynamics, maximum urine flow rate (which may be indicative of the level of urinary tract blockage, if any), and average urine flow rate. The filtered signals can be correlated to urine flow levels. In order to customize this information, the patient's height, weight, body mass index, blood pressure and other data of his medical history can be uploaded into the processor. A database of urine flow data generated by patients who are classified a being healthy as well as from those who are suffering from various conditions that result in abnormal urine flow can be stored in the processor's calibration circuit. Once a patient's voiding patterns are established with the device, they can be compared to voiding patterns in the database and appropriate information displayed.

Figure 10A:
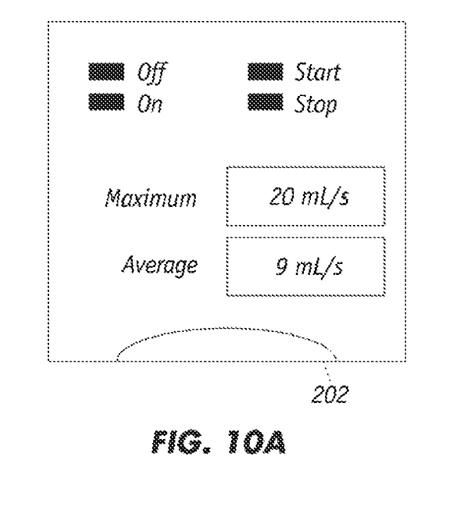
FIGS. 10A and 10B depict urine flow monitoring devices with display panels.
Figure 10B:
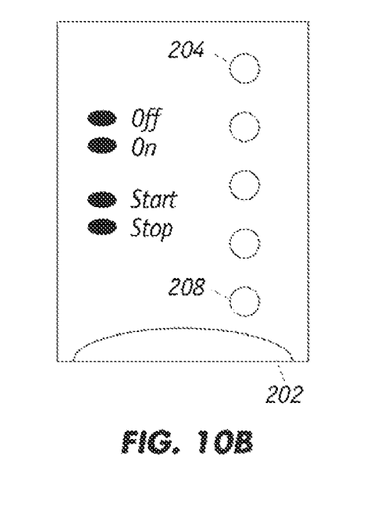
Figure 11:
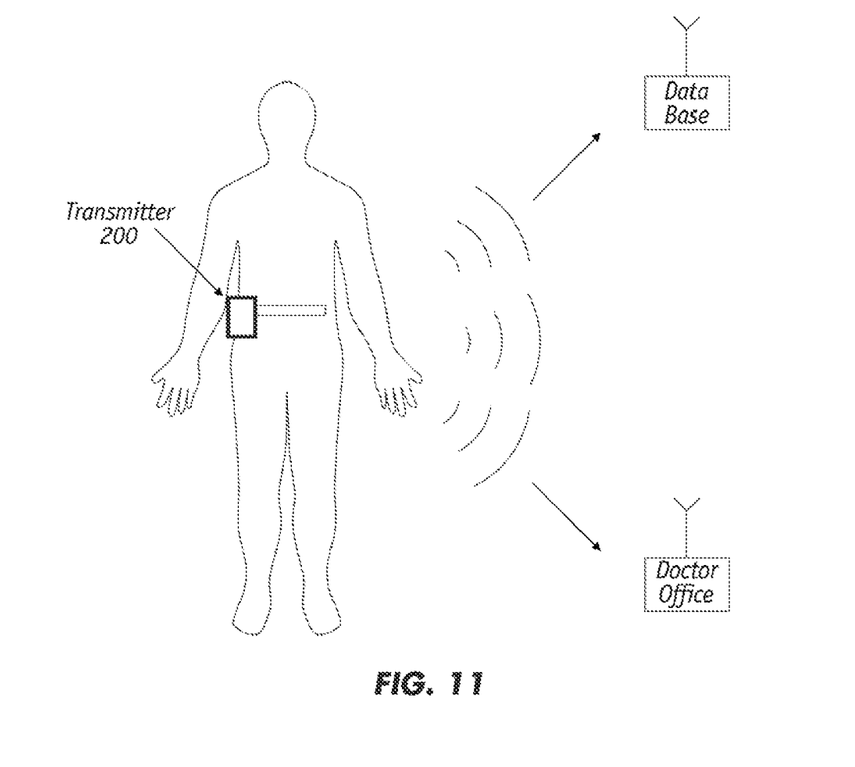
FIG. 11 illustrates the operations of the urine flow monitoring device transmitting data.

As shown in FIG. 10A, the urine flow monitoring device preferably includes a liquid crystal display unit with a urinary flow indicator on the face of the case surface just above microphone 202. In this particular configuration, the indicator presents the maximum and average urine flow readings. In another configuration as shown in FIG. 108, the indicator informs the user of the results qualitatively with a series of color LEDs, 204 through 208. For example, in presenting flow level measurements, the colors can vary from green (as illuminated by LED 204), turquoise, yellow, orange, to red (LED 208), which correspond approximately to normal or "healthy" condition to abnormal or "unhealthy" condition. As is apparent, the urinary flow indicator can be designed to display additional information that is generated by the processor. The urine flow-monitoring device can also be equipped with a transmitter 200 as shown in FIG. 11, which transmits data to a database and to physician's office. Clinicians will thus have ready access to a patient's urine flow pattern history.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. An apparatus for measuring urine flow received by a liquid containing receptacle as a male patient urinates that comprises:
   a microphone dissociated from the patient and positioned to detect acoustical sound that is generated as urine which has been voided from the patient impacts a surface of the liquid that is in the receptacle and converting the acoustical sound into electrical signals;
   an amplifier connected to the microphone to amplify electrical signals therefrom; and
   means for analyzing signal components to generate a measure of a rate of urine flow impacting the surface of the liquid.

2. The apparatus of claim 1 further comprising a filter, for extracting filtered signals, which is positioned between the amplifier and the means for analyzing signals components.

3. The apparatus of claim 2 comprising a plurality of monitoring channels.

4. The apparatus of claim 3 wherein each monitoring channel includes a plurality of filters.

5. The apparatus of claim 2 wherein the filtered signals comprise a measurement signal that is sensitive to urine flow level.

6. The apparatus of claim 5 comprising two or more measurement channels.

7. The apparatus of claim 5 wherein the filtered signals comprise measurement signals that have frequencies in the range from 250 to 550 Hz.

8. The apparatus of claim 3 wherein the filtered signals comprise reference signals that are insensitive to urine flow level.

9. The apparatus of claim 8 comprising two or more reference channels.

10. The apparatus of claim 9 wherein the reference signals have frequencies in the range from 1000 to 1200 Hz, 2000 to 2200 Hz, and/or 4400 to 4600 Hz.

11. The apparatus of claim 1 comprising a plurality of microphones.

12. The apparatus of claim 1 wherein the means for analyzing signal components yield urine flow data that is selected from the group consisting of average flow rate, maximum flow rate, time to maximum, total void volume, total void time, flow dynamics, and combinations thereof.

13. The apparatus of claim 1 comprising an analogue-to-digital converter, for converting amplified electrical signals into digital form, which is positioned between the amplifier and the means for analyzing signal components.

14. A system for analyzing urinary flow patterns of a male patient as he voids that comprises:
   a microphone dissociated from the patient and that is configured for converting acoustic energy, that is generated as urine which has been voided from the patient impacts a surface that is located externally from the patient, into electrical signals;
   an amplifier connected to the microphone to amplify electrical signals therefrom; and
   means for analyzing signal components to measure a rate of urinary flow impacting the surface.

15. The system of claim 14 comprising a filter, for filtering the amplified electrical signals, which is positioned between the amplifier and the means for analyzing signal components, to yield filtered signal components that are indicative of urinary flow patterns.

16. The system of claim 15 wherein the filtered signal components comprise measurement signals that have a frequency in the range from 250 to 550 Hz.

17. The system of claim 15 wherein the filter further yields filtered reference signals that are insensitive to urinary flow levels.

18. The system of claim 17 wherein the filtered reference signals have frequencies in the range from 1000 to 1200 Hz, 2000 to 2200 Hz, and/or 4400 to 4600 Hz.

19. The system of claim 14 comprising an analogue-to-digital converter, for converting amplified signals into digital form, which is positioned between the amplifier and the means for analyzing signal components.

20. The system of claim 15 wherein the means for analyzing signal components yield urine flow data that is selected from the group consisting of average flow rate, maximum flow rate, time to maximum, total void volume, total void time, flow dynamics, and combinations thereof.

21. A portable device designed to be worn on a male patient for measuring urinary flow patterns as he voids that comprises:
   a microphone dissociated from the patient and that is configured for converting acoustic energy, that is generated as urine which has been voided from the patient impacts a surface that is located externally from the patient, into electrical signals;
   an amplifier connected to the microphone to amplify electrical signals to yield amplified electrical signals; and
   means for processing signal components to generate signals that are representative of a rate of urinary flow impacting the surface.

22. The portable device of claim 21 comprising a filter for, filtering the amplified electrical signals, which is positioned between the amplifier and the means for processing signal components, to yield filtered signal components that are indicative of urinary flow patterns.

23. The portable device of claim 21 comprising an analogue-to-digital converter, for converting the amplified electrical signals into digital form, which is positioned between the amplifier and the means for processing signal components.

24. The portable device of claim 21 further comprising a transmitter to transmit signals, which are representative of urinary flow data, for remote recording and assess.

25. The portable device of claim 21 further comprising an indicator to display the urinary flow data.

26. A method for measuring urinary flow from a male patient as he voids that comprises the steps of:
   (a) detecting acoustic energy that is generated as urine which has been voided impacts a liquid surface that is located externally from the patient using a microphone that is dissociated from the patient;
   (b) converting the acoustic into electrical signals; and (c) processing the electrical signals to generate output signals that represent a measure of a rate of urinary flow impacting the liquid surface.

27. The method of claim 26 further comprising the step of separating the electrical signal into spectral components of various frequencies before the spectral components are processed in step (c).

28. The method of claim 27 wherein the first spectral component has a frequency in the range of 250 to 550 Hz and the second spectral component has a frequency in the range of 1000 to 1200 Hz, 2000 to 2200 Hz, and/or 4400 to 4600 Hz.

29. The method of claim 26 wherein the electrical signals are analogue signals that are converted into digital form before being processed in step (c).

30. The apparatus of claim 1 comprising a plurality of monitoring channels.

31. The apparatus of claim 30 wherein the amplifier generates amplified electrical signals that are split to form the plurality of monitoring channels.

* * * * *